(12) United States Patent
Ferri

(10) Patent No.: US 7,131,939 B2
(45) Date of Patent: Nov. 7, 2006

(54) TOE STRETCHER

(76) Inventor: Frederic Ferri, 1013 Fountain St., Ann Arbor, MI (US) 48103

( * ) Notice: Subject to any disclaimer, the term of this patent is extended or adjusted under 35 U.S.C. 154(b) by 310 days.

(21) Appl. No.: 10/687,354

(22) Filed: Oct. 17, 2003

(65) Prior Publication Data

US 2005/0085756 A1    Apr. 21, 2005

(51) Int. Cl.
*A63B 71/00* (2006.01)
(52) U.S. Cl. .............. 482/148; 15/167.3; 132/75.6; 482/79
(58) Field of Classification Search ............ 482/48, 482/148, 47, 49; D21/685; 15/167.3; 132/73, 132/76.4, 75.6; D28/56–57, 59, 61; 30/26
See application file for complete search history.

(56) References Cited

U.S. PATENT DOCUMENTS

| | | | | |
|---|---|---|---|---|
| 5,039,093 A | * | 8/1991 | Collier | 482/124 |
| 5,062,625 A | * | 11/1991 | Vonk | 482/48 |
| 5,136,911 A | * | 8/1992 | Wyss | 84/468 |
| 5,374,226 A | * | 12/1994 | Grahm | 482/47 |
| 5,466,202 A | * | 11/1995 | Stern | 482/47 |
| 5,723,785 A | * | 3/1998 | Manning | 73/379.03 |
| D439,704 S | * | 3/2001 | Ikeda | D28/57 |
| 6,228,001 B1 | * | 5/2001 | Johnson et al. | 482/48 |
| 6,352,069 B1 | * | 3/2002 | Kraus et al. | 123/622 |
| 6,481,443 B1 | * | 11/2002 | Moore-Johnson et al. | 132/73 |
| D481,828 S | * | 11/2003 | Goldberg et al. | D28/56 |
| 6,817,967 B1 | * | 11/2004 | Ott et al. | 482/48 |
| 6,941,954 B1 | * | 9/2005 | Belcher | 132/73 |

* cited by examiner

Primary Examiner—Lori Amerson
(74) Attorney, Agent, or Firm—Tope-McKay & Assoc.

(57) ABSTRACT

The present invention relates to an exercise tool. More particularly, it relates to an exercise tool specifically devised as a toe stretcher to align, separate, and stretch toes. The toe stretcher comprises a frame with a separator for separating a plurality of toes. The frame further includes holes or indentations for placement of the toes. Additionally, the frame is flexible, allowing a user to easily manipulate the toe stretcher and place it on the user's toes, effectively separating and stretching toes. Furthermore, the toe stretcher may be attached with a footwear, allowing a user to not only stretch toes, but to also use the toe stretcher as a footwear.

23 Claims, 9 Drawing Sheets

TOE STRETCHER

FIELD OF INVENTION

The present invention relates to an exercise tool, and more particularly, to an exercise tool devised as a toe stretcher to align, separate, and stretch toes.

BACKGROUND OF INVENTION

Exercise tools have long been known in prior art. Sports and yoga enthusiasts have devised a myriad of stretching tools. Recently, such stretching tools have been applied to not only stretch larger muscles, but also toes. Several toe stretchers have been invented, where a user places a toe stretcher between the user's toes, effectively stretching the toes.

A few advantages of a toe stretcher are that it increases foot strength, increases toe and ankle flexibility, improves arches, and stretches Achilles' tendons. Although toe stretchers devised to date have substantially filled this need, they are difficult to use. Existing toe stretchers consist of a frame with five holes for toe insertion. The five holes are substantially circular, with each circle being sealed around its perimeter. Because each circle is sealed, inserting all five toes has been problematic, making it difficult to put the toe stretcher on and take it off.

Therefore, it can be appreciated that there exists a continuing need for a new and improved toe stretcher that is easier to put on and take off. In this regard, the present invention substantially fulfills this need.

SUMMARY OF INVENTION

The present invention relates to an exercise tool, and more particularly, to an exercise tool devised as a toe stretcher to align, separate, and stretch toes. The toe stretcher comprises a frame with a separator for separating a plurality of toes, whereby a user may place the toe stretcher on the plurality toes and effectively separate and stretch the toes.

In another aspect, the frame comprises a top portion, a bottom portion, a front portion, and a back portion. In this aspect, the frame further includes a plurality of holes through the frame for insertion of a plurality of toes, wherein each hole in the plurality of holes includes an entrance into the back portion, an exit from the front portion, and surrounding walls connecting the entrance with the exit. Additionally, the surrounding walls in at least one hole in the plurality of holes is continuous and thereby sealed and the surrounding walls in at least one other hole in the plurality of holes is non-continuous and thereby not sealed, serving as an openable toe hole allowing for easy insertion of a toe.

Furthermore, the openable toe hole is sealed through use of an enclosure. The enclosure is selected from a group consisting of Velcro, snaps, an elastic band, hole and pin, and a male/female joint system.

In another aspect, the toe stretcher further comprises a footwear attached with the bottom portion.

In yet another aspect, the frame comprises an elongated top part connected with an elongated bottom part. In this aspect, the frame further includes a plurality of indentations in both the elongated top part and the elongated bottom part for placement of a plurality of toes, whereby upon placing toes upon the indentations on the elongated bottom part, a user may close the frame by closing the elongated top part upon a top side of a corresponding toe or toes.

Furthermore, the elongated top part is connected with the elongated bottom part through a connector. In another aspect, the connector is a hinge. Additionally, an unconnected portion of the elongated top part and an unconnected portion of the elongated bottom part may be connected through use of an enclosure. It is another aspect of the present invention that the enclosure is selected from a group consisting of Velcro, snaps, an elastic band, hole and pin, and a male/female joint system.

In another aspect, the toe stretcher further comprises a footwear attached with the elongated bottom part.

In another aspect, the frame comprises an elongated top part separated from an elongated bottom part. In this aspect, the frame further includes a plurality of indentations in both the elongated top part and the elongated bottom part for placement of a plurality of toes, whereby upon placing a bottom side of toes upon the indentations on the elongated bottom part, a user may place the elongated top part upon a top side of a corresponding toe or toes and thereby utilize the toe stretcher.

Furthermore, an unconnected portion of the elongated top part and an unconnected portion of the elongated bottom part may be connected through use of an enclosure. The enclosure is selected from a group consisting of Velcro, snaps, an elastic band, hole and pin, and a male/female joint system.

In another aspect, the toe stretcher further comprises a footwear attached with the elongated bottom part.

In another aspect, the frame comprises an elongated bottom part. In this aspect, the frame further includes a plurality of spacing members in the elongated bottom part, thereby creating a plurality of indentations for placement of a plurality of toes. Additionally, at least one spacing member in the plurality of spacing members includes a vertical hole running from a top side of the at least one spacing member to a bottom side of the elongated bottom part, whereby a user may utilize the toe stretcher by placing a bottom side of at least one toe upon a corresponding indentation on the elongated bottom part and by placing at least one spacing member between adjacent toes.

In another aspect, a filament is placed through the vertical hole. The filament is operative as an attachment, whereby a user may place the attachment over a top side of at least one toe and thereby utilize the toe stretcher.

In another aspect, the toe stretcher further comprises footwear attached with the elongated bottom part.

It is another aspect of the present invention to claim a method for forming a toe stretcher connected with a footwear. The method comprises an act of connecting a frame with a footwear. In this aspect, the frame has a separator for separating a plurality of toes whereby a user may place the toe stretcher on the plurality toes and effectively separate and stretch the toes.

In another aspect, in the act of connecting a frame with a footwear, the frame further includes a top portion, a bottom portion, a front portion, and a back portion, where the bottom portion of the frame is connected with the footwear. In this aspect, the frame further includes a plurality of holes for insertion of a plurality of toes, where each hole has an entrance on the back portion, an exit on the front portion, and surrounding walls connecting the entrance with the exit. Additionally, the surrounding walls in at least one hole in the plurality of holes is continuous and thereby sealed and the surrounding side walls in at least one other hole in the plurality of holes is non-continuous and thereby not sealed, serving as an openable toe hole allowing for easy insertion of a corresponding toe or toes.

In another aspect, in the act connecting a frame with a footwear, the openable toe hole is sealed through use of an enclosure. The enclosure is selected from a group consisting of Velcro, snaps, an elastic band, hole and pin, and a male/female joint system.

Additionally, in the act of connecting a frame with a footwear, the bottom portion is integrally molded with the footwear.

In another aspect, in the act of connecting a frame with a footwear, the frame and the footwear are separately formed and the act of connecting is performed by attaching the frame with the footwear.

In yet another aspect, in the act of connecting a frame with a footwear, the frame further includes an elongated top part connected with an elongated bottom part, where the elongated bottom part of the frame is connected with the footwear. In this aspect, the frame further includes a plurality of indentations included in both the elongated top part and the elongated bottom part for placement of a plurality of toes, whereby upon placing a bottom side of toes upon the indentations on the elongated bottom part, a user may close the frame by closing the elongated top part upon a top side of a corresponding toe or toes.

Additionally, in the act of connecting a frame with a footwear, the elongated top part is connected with the elongated bottom part through a connector such as a hinge.

Furthermore, in the act of connecting a frame with a footwear, an unconnected portion of the elongated top part and an unconnected portion of the elongated bottom part are connected through use of an enclosure.

In another aspect, in the act of connecting a frame with a footwear, the enclosure is selected from a group consisting of Velcro, snaps, an elastic band, hole and pin, and a male/female joint system.

Additionally, in the act of connecting a frame with a footwear, the elongated bottom part is integrally formed with the footwear.

In yet another aspect, in the act of connecting a frame with a footwear, the frame and the footwear are separately formed and the act of connecting is performed by attaching the frame with the footwear.

Furthermore, in the act of connecting a frame with a footwear, an unconnected portion of the elongated top part and an unconnected portion of the elongated bottom part are connected through use of an enclosure. The enclosure is selected from a group consisting of Velcro, snaps, an elastic band, hole and pin, and a male/female joint system.

In yet another aspect, in the act of connecting a frame with a footwear, the frame further includes an elongated top part separated from an elongated bottom part, where the elongated bottom part is connected with the footwear. The frame further includes a plurality of indentations in both the elongated top part and the elongated bottom part for placement of a plurality of toes, whereby upon placing toes upon the indentations on the elongated bottom part, a user may place the elongated top part upon a top side of a corresponding toe or toes and thereby complete the frame and utilize the toe stretcher.

Additionally, in the act of connecting a frame with a footwear, an unconnected portion of the elongated top part and an unconnected portion of the elongated bottom part may be connected through use of an enclosure. The enclosure is selected from a group consisting of Velcro, snaps, an elastic band, hole and pin, and a male/female joint system.

Furthermore, in the act of connecting a frame with a footwear, the elongated bottom part is integrally molded with the footwear.

In another aspect, in the act of connecting a frame with a footwear, the frame and the footwear are separately formed and the act of connecting is performed by attaching the frame with the footwear.

In yet another aspect, in the act of connecting a frame with a footwear, the frame further includes an elongated bottom part with a plurality of spacing members creating a plurality of indentations for placement of a plurality of toes. At least one spacing member in the plurality of spacing members includes a vertical hole running from a top side of the at least one spacing member to a bottom side of the elongated bottom part, whereby a user may utilize the toe stretcher by placing a bottom side of at least one toe upon a corresponding indentation on the elongated bottom part and by placing at least one spacing member between adjacent toes.

Additionally, in the act of connecting a frame with a footwear, a filament is placed through the vertical hole. The filament is operative as an enclosure, whereby a user may place the enclosure over a top side of at least one toe and thereby utilize the toe stretcher.

In another aspect, in the act of connecting a frame with a footwear, the frame and the footwear are separately formed and the act of connecting is performed by attaching the frame with the footwear.

In yet another aspect, in the act of connecting a frame with a footwear, the elongated bottom part is integrally molded with the footwear.

BRIEF DESCRIPTION OF THE DRAWINGS

The nature of the toe stretchers described herein will be readily apparent in the following drawings, in which.

DETAILED DESCRIPTION

The present invention relates to an exercise tool, and more particularly, to an exercise tool specifically devised as a toe stretcher to align, separate, and stretch toes.

The following description, taken in conjunction with the referenced drawings, is presented to enable one of ordinary skill in the art to make and use the invention. Various modifications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein. Furthermore it should be noted that unless explicitly stated otherwise, the figures included herein are illustrated diagrammatically and without any specific scale, as they are provided as qualitative illustrations of the concept of the present invention.

Figure 1:
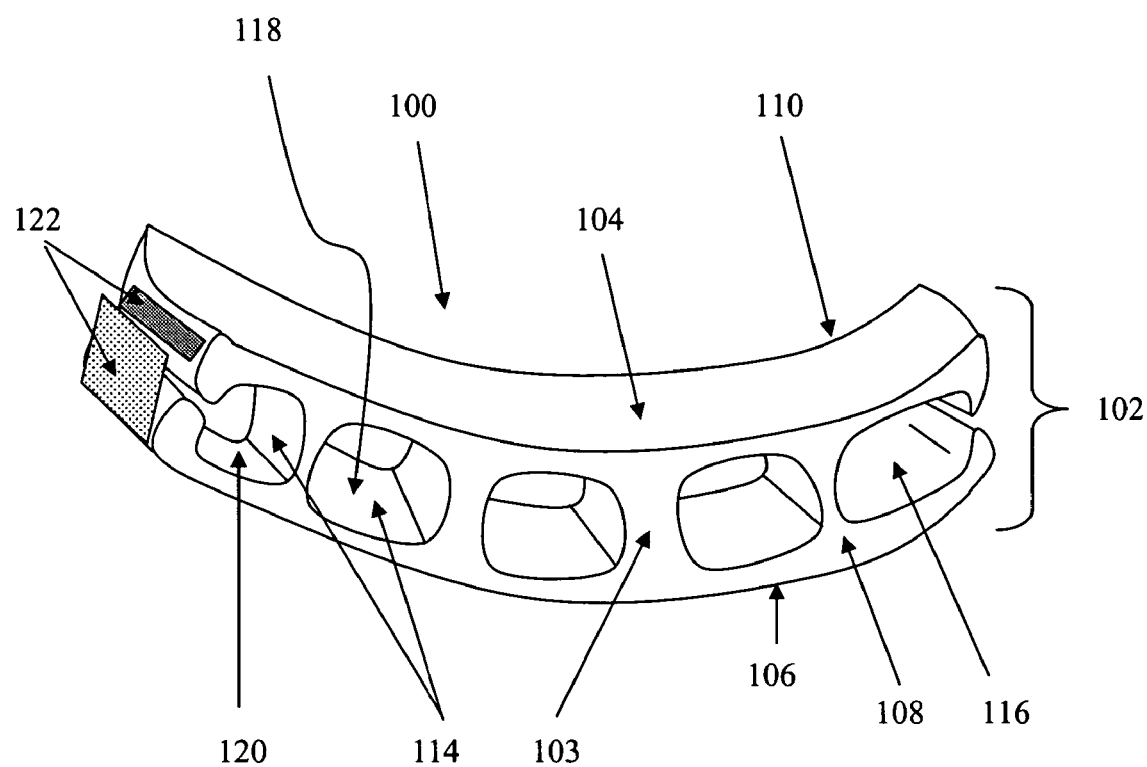
FIG. 1 is a front perspective view of a toe stretcher according to the present invention.

A toe stretcher 100 according to the present invention is shown in FIG. 1. The toe stretcher 100 comprises a frame 102 with a separator 103 for separating a plurality of toes. The frame 102 may be constructed of any suitable material, non-limiting examples of which include plastic, silicone, and cork. Additionally, the frame 102 may be optionally inflatable or filled with a fluid. When inflatable, the frame 102 may be inflatable to various pressures. Furthermore, the frame 102 may be formed through any suitable means for forming a frame 102, non-limiting examples of which include injection molding, cast molding, compression molding, and extrusion molding. The frame 102 has a top portion 104, a bottom portion 106, a front portion 108, and a back portion 110.

Included in the frame 102 are a plurality of holes 114, each configured for insertion of a toe. Each hole has an entrance on the back portion 110, an exit on the front portion 108, and surrounding walls 116. The surrounding walls 116 may be flat, curved or any other suitable shape to accommodate a toe. Additionally, the surrounding walls 116 in at least one hole of the plurality of holes 114 is continuous and thereby sealed, serving as a sealed toe hole 118. Additionally, the surrounding walls 116 in at least one other hole in the plurality of holes 114 is non-continuous and thereby not sealed, serving as an openable toe hole 120 allowing for easy insertion of a corresponding toe or toes.

The openable toe hole 120 may be sealed through use of an enclosure 122. Furthermore, the enclosure 122 may be any suitable device or mechanim for attaching one medium with another, non-limiting examples of which include Velcro, snaps, an elastic band, hole and pin, and a male/female joint system.

Figure 2:
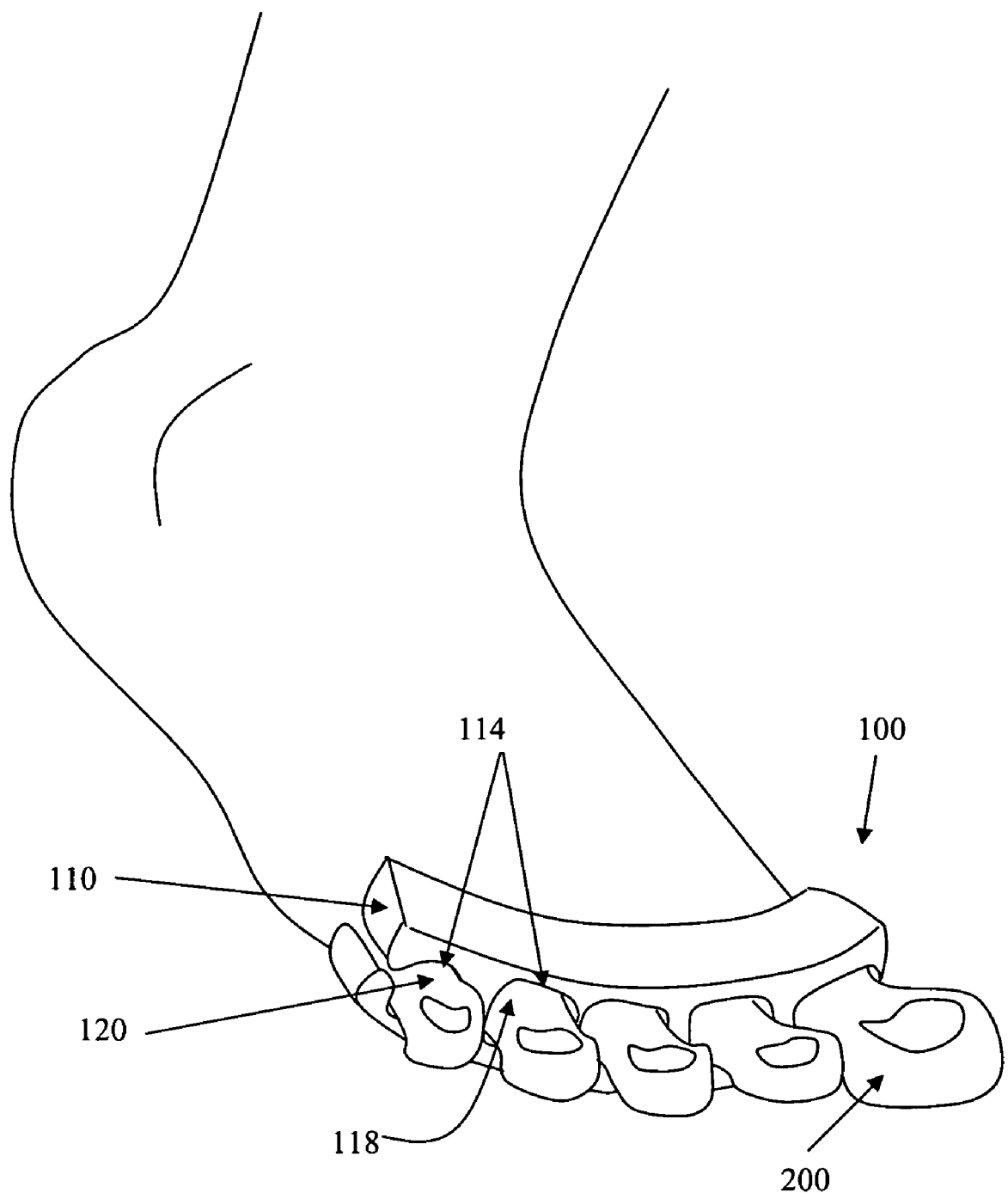
FIG. 2 is a front perspective view of a toe stretcher according to the present invention, with toes inserted therein.

A toe stretcher 100 with toes 200 inserted therein, is illustrated in FIG. 2. Although at least one hole in the plurality of holes 114 serves as a sealed toe hole 118, at least one other hole in the plurality of holes 114 is not sealed and serves as an openable toe hole 120. Because the openable toe hole 120 is not sealed, the toe stretcher 100 may be easily distorted and manipulated to allow easy insertion of toes 200 therein. The significance of the openable toe hole 120 is that without the openable toe hole 120, the toe stretcher is not easily manipulated, thereby making it difficult to utilize existing toe stretchers.

Figure 3:
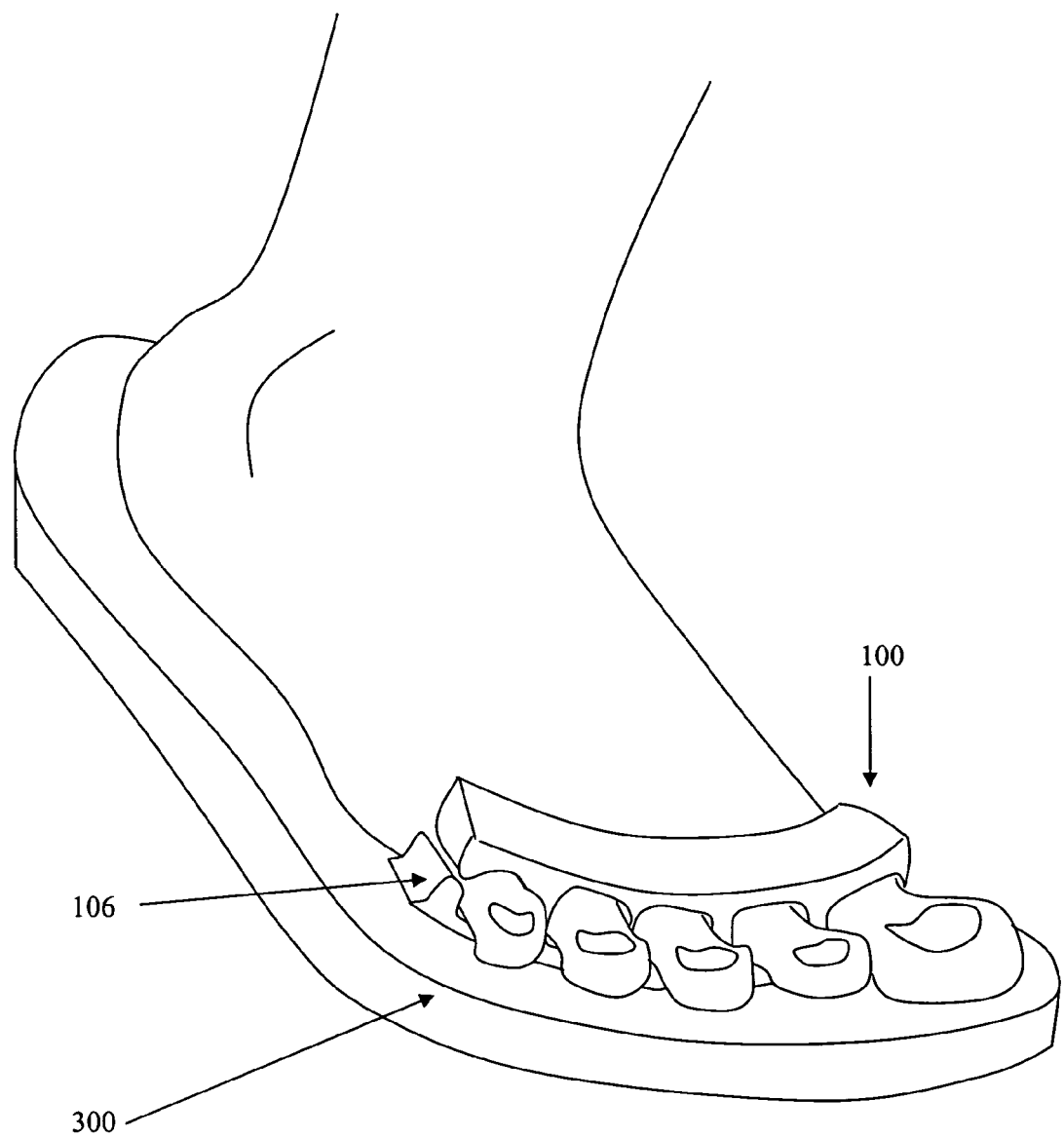
FIG. 3 is a front perspective view of the toe stretcher of FIG. 1, with a footwear attached.

The toe stretcher 100 of FIG. 1 is shown in FIG. 3 attached with a footwear 300. As illustrated, the bottom portion 106 is attached with the footwear 300. The bottom portion 106 may be integrally molded with the footwear 300 or separately formed and thereafter attached with the footwear 300. When separately formed and attached, the bottom portion 106 may be attached with the footwear 300 through any suitable device or mechanism for attaching one medium with another, non-limiting examples of which include Velcro, an adhesive, snaps, an elastic band, hole and pin, and a male/female joint system. Furthermore, the footwear 300 may be any suitable footwear, a non-limiting example of which includes a sandal.

Figure 4:
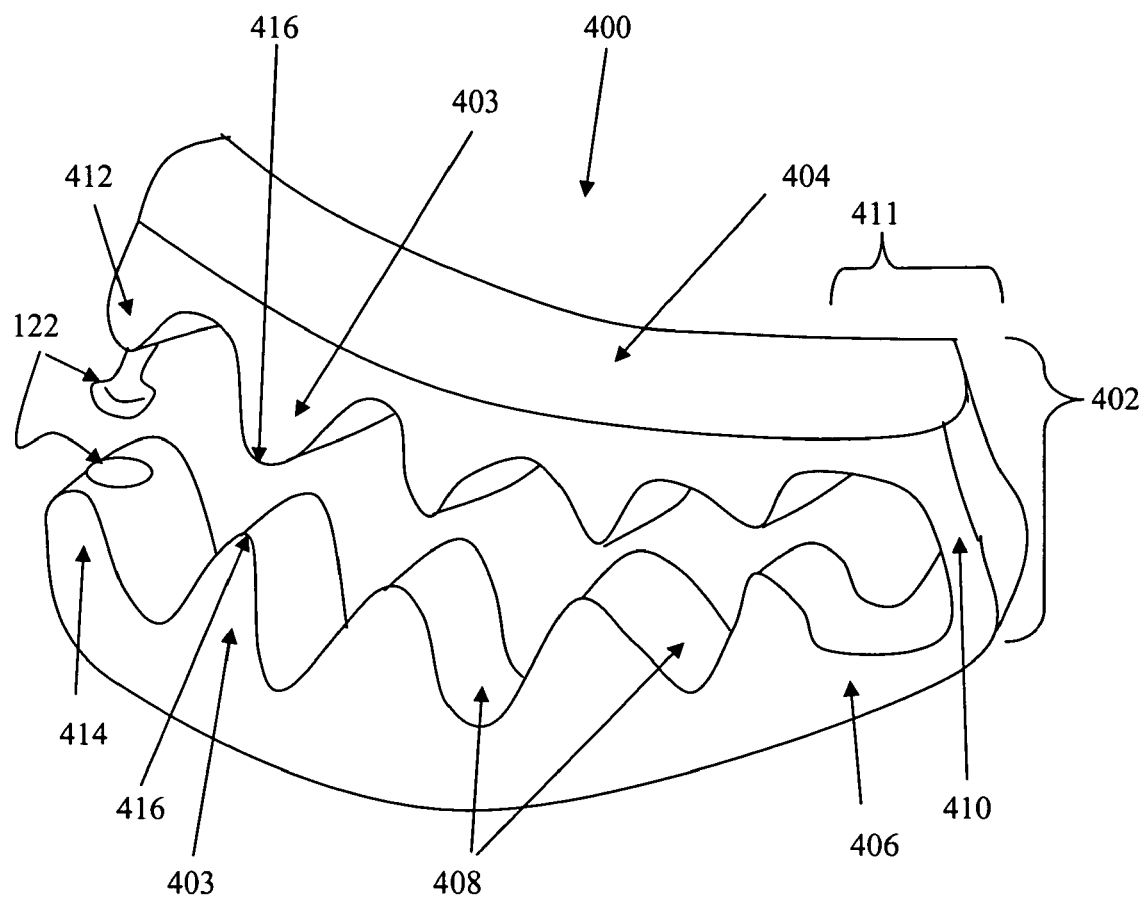
FIG. 4 is a front perspective view illustrating a toe stretcher of the present invention, where an elongated top part is connected with an elongated bottom part.

FIG. 4 illustrates another aspect of the toe stretcher 400 of the present invention. In this aspect, the toe stretcher 400 comprises a frame 402 with a separator 403 for separating a plurality of toes. The frame 402 may be constructed of any suitable material, non-limiting examples of which include plastic, silicone, and cork. Additionally, the frame 402 may be optionally inflatable or filled with a fluid. When inflatable, the frame 402 may be inflatable to various pressures. Furthermore, the frame 402 may be formed through any suitable means for forming a frame 402, non-limiting examples of which include injection molding, cast molding, compression molding, and extrusion molding.

The frame 402 has an elongated top part 404 and an elongated bottom part 406. The elongated top part 404 and the elongated bottom part 406 each have a plurality of indentations 408 for placement of a plurality of toes. The plurality of indentations 408 may be flat, curved or any other suitable shape to accommodate a toe.

Figure 5:
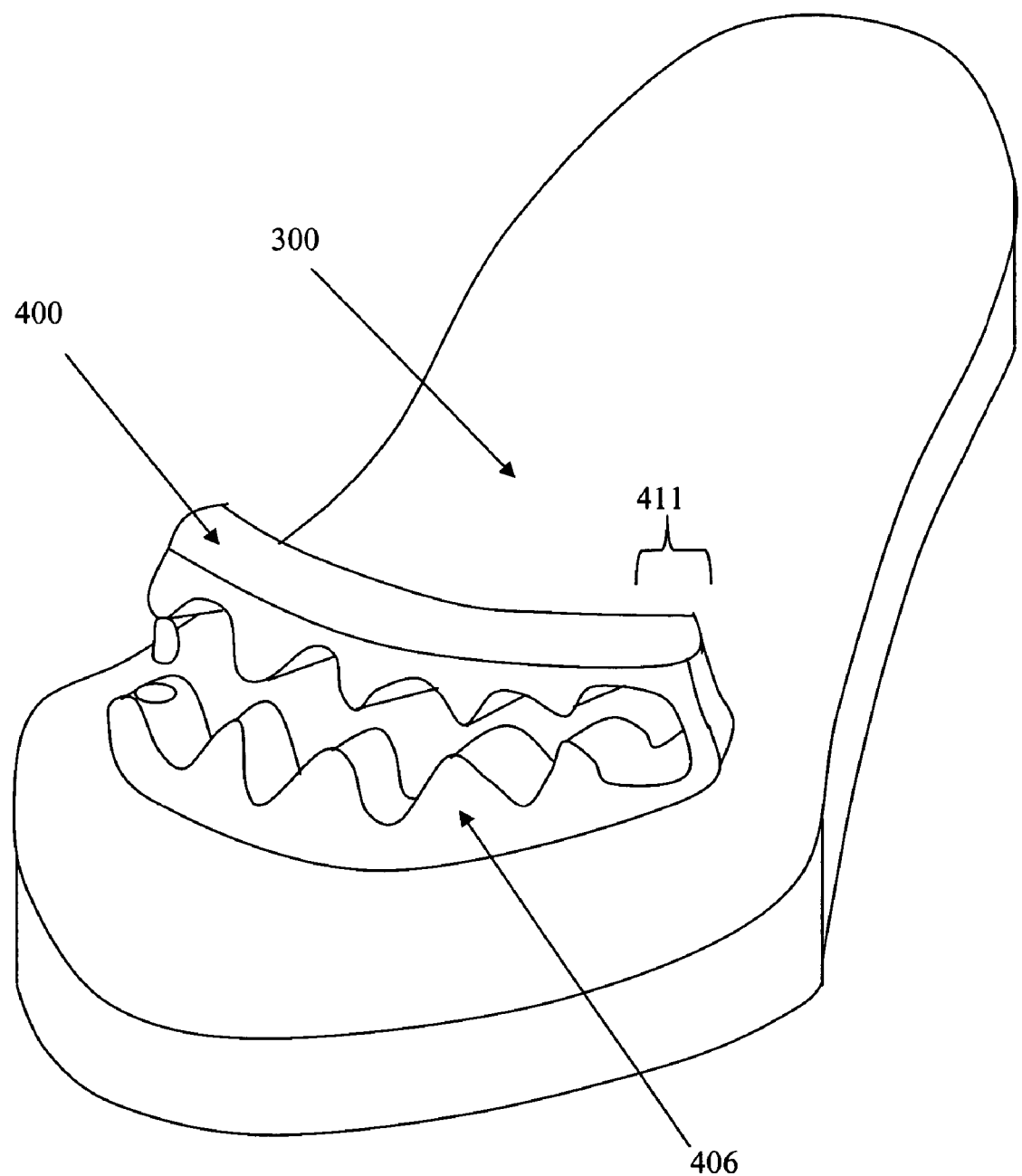
FIG. 5 is a front perspective view of the toe stretcher of FIG. 4, with a footwear attached.

The elongated top part 404 is connected with the elongated bottom part 406 through a connector 410. The connector 410 may be located at any suitable location for connecting the elongated top part 404 with the elongated bottom part 406, non-limiting examples of which include being connected on a big-toe indentation side, on a little-toe indentation side, and between two toe indentations. For example, FIGS. 4 and 5 illustrate the connector 410 located on little-toe indentation side 411. Additionally, the connector 410 may be any suitable device or mechanism for connecting two mediums together, a non-limiting example of which includes a hinge. Through use of the connector 410, a user may place a bottom side of the toes upon the plurality of indentations 408 and close the frame 402 by closing the elongated top part 404 upon a top side of a corresponding toe or toes.

Additionally, an unconnected portion of the elongated top part 412 and an unconnected portion of the elongated bottom part 414 may be connected through use of an enclosure 122. The enclosure 122 may be located at any unconnected portion of the elongated top part 412 and respective unconnected portion of the elongated bottom part 414. For example and as shown in FIG. 4, the enclosure 122 may be located at unconnected end portions of the elongated bottom top part 412 and elongated bottom part 414. As an alternative example, the enclosure 122 may be located at unconnected tip portions 416 of corresponding separators 403. The enclosure 122 may be any suitable device or mechanism for attaching one medium with another, non-limiting examples of which include Velcro, snaps, an elastic band, hole and pin, and a male/female joint system.

The toe stretcher 400 of FIG. 4 is shown in FIG. 5 attached with a footwear 300. As illustrated, the elongated bottom part 406 is attached with the footwear 300. The elongated bottom part 406 may be integrally molded with the footwear 300 or separately formed and thereafter attached with the footwear 300. When separately formed and attached, the elongated bottom part 406 may be attached with the footwear 300 through any suitable mechanism or device for attaching one medium with another, non-limiting examples of which include Velcro, an adhesive, snaps, an elastic band, hole and pin, and a male/female joint system. Furthermore, the footwear 300 may be any suitable footwear, a non-limiting example of which includes a sandal.

Figure 6:
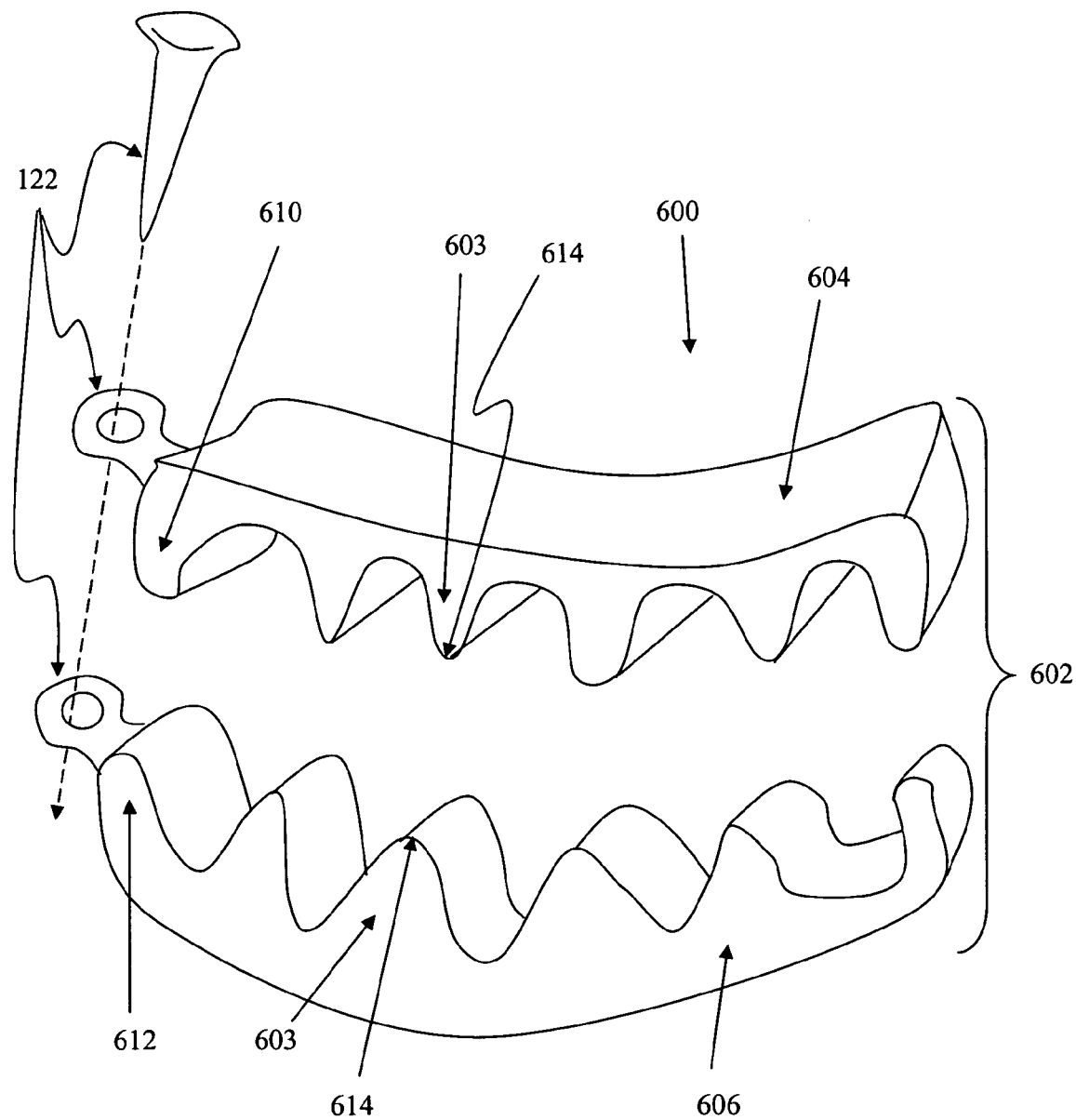
FIG. 6 is a front perspective view illustrating a toe stretcher of the present invention, where an elongated top part is separate and not connected with an elongated bottom part.

FIG. 6 illustrates another aspect of the toe stretcher 600 of the present invention. In this aspect, the toe stretcher comprises a frame 602 with a separator 603 for separating a plurality of toes. The frame 602 may be constructed of any suitable material, non-limiting examples of which include plastic, silicone, and cork. Additionally, the frame 602 may be optionally inflatable or filled with a fluid. When inflatable, the frame 602 may be inflatable to various pressures. Furthermore, the frame 602 may be formed through any suitable means for forming a frame 602, non-limiting examples of which include injection molding, cast molding, compression molding, and extrusion molding.

Additionally, the frame 602 has an elongated top part 604 and an elongated bottom part 606. The elongated top part 604 and the elongated bottom part 606 each have a plurality of indentations 608 for placement of a plurality of toes. A key difference between the frame 602 in this aspect and that as illustrated in FIG. 4, is that in this aspect, the elongated top part 604 is not connected with the elongated bottom part 606. An unconnected portion of the elongated top part 610 and an unconnected portion of the elongated bottom part 612 may be connected through use of an enclosure 122. The enclosure 122 may be located at any unconnected portion of the elongated top part 610 and corresponding unconnected portion of the elongated bottom part 612. For example and as shown in FIG. 6, the enclosure 122 may be located at unconnected end portions of the elongated bottom top part 610 and elongated bottom part 612. As an alternative example, the enclosure 122 may be located at unconnected tip portions 614 of corresponding separators 603. The enclosure 122 may be any suitable mechanism or device for attaching one medium with another, non-limiting examples of which include Velcro, snaps, an elastic band, hole and pin, and a male/female joint system.

Figure 7:
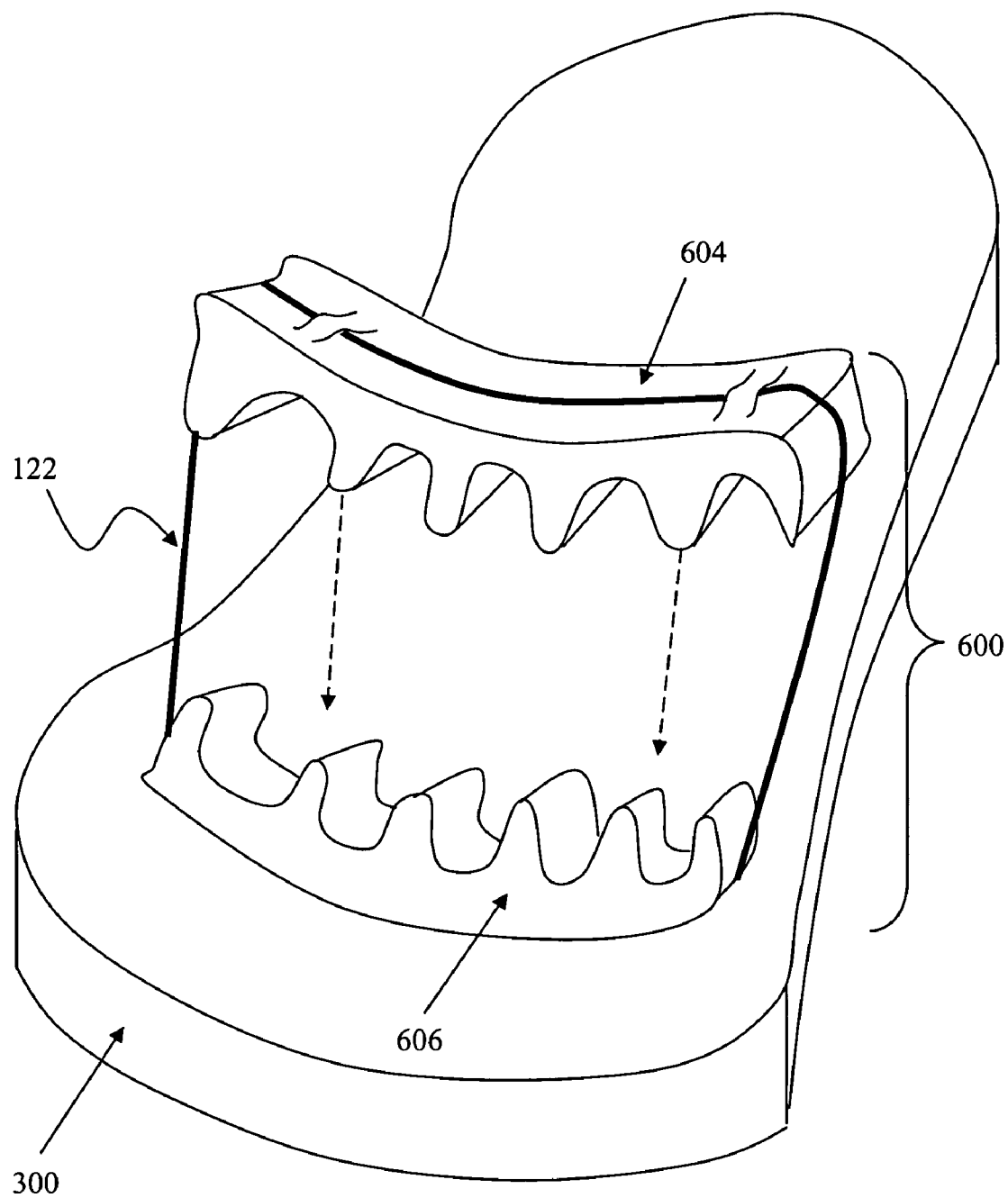
FIG. 7 is a front perspective view of the toe stretcher of FIG. 6, with a footwear attached.

The toe stretcher 600 of FIG. 6 is shown in FIG. 7 attached with a footwear 300. As illustrated, the elongated bottom part 606 is attached with the footwear 300. The elongated bottom part 606 may be integrally molded with the footwear 300 or separately formed and thereafter attached with the footwear 300. When separately formed and attached, the elongated bottom part 606 may be attached with the footwear 300 through any suitable mechanism or device for attaching one medium with another, non-limiting examples of which include Velcro, an adhesive, snaps, an elastic band, hole and pin, and a male/female joint system. Furthermore, the footwear 300 may be any suitable footwear, a non-limiting example of which includes a sandal.

As illustrated, the elongated top part 604 may be held together with the elongated bottom part 606 through use of an enclosure 122. In this particular illustration, the enclosure 122 is an elastic band pulling the elongated top part 604 towards the elongated bottom part 606. When the enclosure 122 is an elastic band, the band may be attached with the toe stretcher through any suitable mechanism or device. For example, the band may integrally attached, or alternatively, held in a groove like an o-ring.

Figure 8:
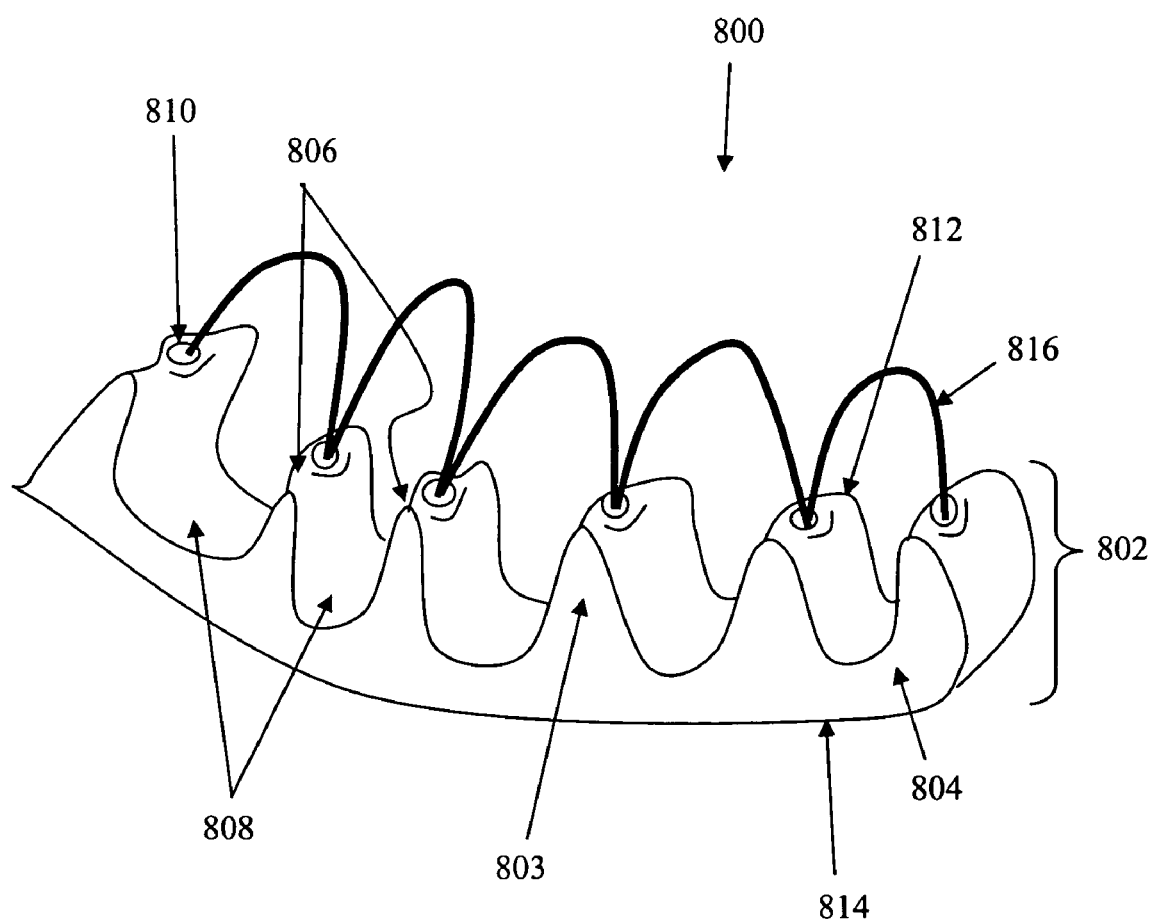
FIG. 8 is a front perspective view illustrating a toe stretcher of the present invention, where spacing members in an elongated bottom part include a vertical hole running from a top side of at least one spacing member to a bottom side of the elongated bottom part.

FIG. 8 illustrates yet another aspect of the toe stretcher 800. In this aspect, the toe stretcher 800 comprises a frame 802 with a separator 803 for separating a plurality of toes. The frame 802 may be constructed of any suitable material, non-limiting examples of which include plastic, silicone, and cork. Additionally, the frame 802 may be optionally inflatable or filled with a fluid. When inflatable, the frame 802 may be inflatable to various pressures. Furthermore, the frame 802 may be formed through any suitable means for forming a frame 802, non-limiting examples of which include injection molding, cast molding, compression molding, and extrusion molding.

The frame 802 comprises an elongated bottom part 804 that includes a plurality of spacing members 806. The plurality of spacing members 806 create a plurality of indentations 808 for placement of a plurality of toes. At least one spacing member in the plurality of spacing members 806 includes a vertical hole 810 running from a top side 812 of the at least one spacing member to a bottom side 814 of the elongated bottom part 804. A user may utilize the toe stretcher 800 by placing a bottom side of at least one toe upon a corresponding indentation on the elongated bottom part 804 and by placing at least one spacing member 806 between adjacent toes.

Additionally, a filament 816 may be placed through the vertical hole 810. The filament may be any suitably elongated material, non-limiting examples of which include an elastic band, string, and ribbon. The filament 816 is operative as an attachment, attaching the elongated bottom part 804 with a bottom side of at least one toe, or when flipped over, with a top side of at least one toe. Accordingly, a user may place the filament 816 over at least one toe and thereby utilize the toe stretcher.

Figure 9:
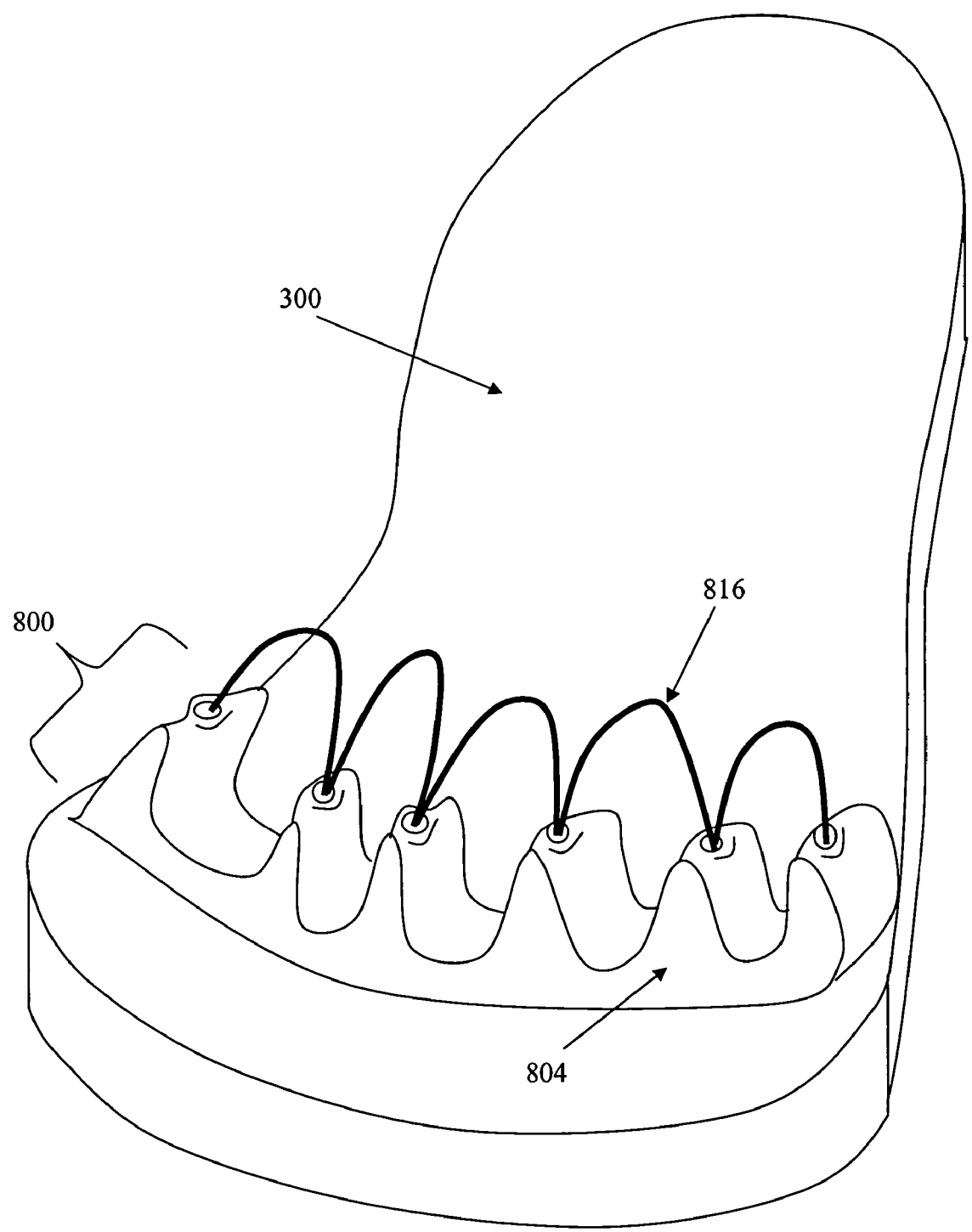
FIG. 9 is a front perspective view of the toe stretcher of FIG. 8, with a footwear attached.

The toe stretcher 800 of FIG. 8 is shown in FIG. 9 attached with a footwear 300. As illustrated, the elongated bottom part 804 is attached with the footwear 300. The elongated bottom part 804 may be integrally molded with the footwear 300 or separately formed and thereafter attached with the footwear 300. When separately formed and attached, the elongated bottom part 804 may be attached with the footwear 300 through any suitable mechanism or device for attaching one medium with another, non-limiting examples of which include Velcro, an adhesive, snaps, an elastic band, hole and pin, and a male/female joint system. Furthermore, the footwear 300 may be any suitable footwear, a non-limiting example of which includes a sandal.

In this particular illustration, the filament 816 is positioned such that it may be placed over at least one toe in order to keep the footwear 300 attached with a foot. In an alternative position, the filament 816 may be wrapped around a user's ankle.

What is claimed is:

1. A toe stretcher for stretching toes, comprising:
   a frame with a separator for separating a plurality of toes;
   wherein the frame comprises a top portion, a bottom portion, a front portion, and a back portion, and further includes:
   a plurality of holes through the frame for insertion of a plurality of toes, wherein each hole in the plurality of holes includes an entrance into the back portion, an exit from the front portion, and surrounding walls connecting the entrance with the exit, wherein:
   the surrounding walls in at least one hole in the plurality of holes is continuous and thereby sealed; and
   the surrounding walls in at least one other hole in the plurality of holes is non-continuous and thereby not sealed, serving as an openable toe hole allowing for easy insertion of a toe, whereby a user may place the toe stretcher on the plurality of toes and effectively separate and stretch the toes.

2. A toe stretcher as set forth in claim 1, wherein the openable toe hole is sealed through use of an enclosure.

3. A toe stretcher as set forth in claim 2, wherein the enclosure is selected from a group consisting of Velcro, snaps, an elastic band, hole and pin, and a male/female joint system.

4. A toe stretcher as set forth in claim 3, further comprising a footwear attached with the bottom portion.

5. A toe stretcher as set forth in claim 1, further comprising a footwear attached with the bottom portion.

6. A toe stretcher for stretching toes, comprising:
   a frame with a separator for separating a plurality of toes;
   wherein the frame has an elongated top part connected with an elongated bottom part, and further includes:

a plurality of indentations included in both the elongated top part and the elongated bottom part for placement of a plurality of toes, whereby upon placing toes upon the indentations on the elongated bottom part, a user may close the frame by closing the elongated top part upon a top side of a corresponding toe or toes; and wherein the elongated top part is connected with the elongated bottom part through a connector, whereby a user may place the toe stretcher on the plurality of toes and effectively separate and stretch the toes.

7. A toe stretcher as set forth in claim 6, wherein the connector is a hinge.

8. A toe stretcher as set forth in claim 7, wherein an unconnected portion of the elongated top part and an unconnected portion of the elongated bottom part may be connected through use of an enclosure.

9. A toe stretcher as set forth in claim 8, wherein the enclosure is selected from a group consisting of Velcro, snaps, an elastic band, hole and pin, and a male/female joint system.

10. A toe stretcher as set forth in claim 9, further comprising a footwear attached with the elongated bottom part.

11. A toe stretcher for stretching toes, comprising:
a frame with a separator for separating a plurality of toes;
wherein the frame has an elongated top part connected with an elongated bottom part, and further includes:
a plurality of indentations included in both the elongated top part and the elongated bottom part for placement of a plurality of toes; and
wherein an unconnected portion of the elongated top part and an unconnected portion of the elongated bottom part may be connected through use of an enclosure, whereby upon placing toes upon the indentations on the elongated bottom part, a user may close the frame by closing the elongated top part upon a top side of a corresponding toe or toes, thereby placing the toe stretcher on the plurality of toes to effectively separate and stretch the toes.

12. A toe stretcher as set forth in claim 11, wherein the enclosure is selected from a group consisting of Velcro, snaps, an elastic band, hole and pin, and a male/female joint system.

13. A toe stretcher for stretching toes, comprising:
a frame with a separator for separating a plurality of toes;
wherein the frame has an elongated top part connected with an elongated bottom part, and further includes:
a plurality of indentations included in both the elongated top part and the elongated bottom part for placement of a plurality of toes, and
further comprising a footwear attached with the elongated bottom part, whereby upon placing toes upon the indentations on the elongated bottom part, a user may close the frame by closing the elongated top part upon a top side of a corresponding toe or toes, thereby placing the toe stretcher on the plurality of toes to effectively separate and stretch the toes.

14. A toe stretcher for stretching toes, comprising:
a frame with a separator for separating a plurality of toes;
wherein the frame has an elongated top part separated from an elongated bottom part, and further includes:
a plurality of indentations included in both the elongated top part and the elongated bottom part for placement of a plurality of toes, whereby upon placing a bottom side of toes upon the indentations on the elongated bottom part, a user may place the elongated top part upon a top side of a corresponding toe or toes and thereby utilize the toe stretcher to effectively separate and stretch the toes.

15. A toe stretcher as set forth in claim 14, wherein an unconnected portion of the elongated top part and an unconnected portion of the elongated bottom part may be connected through use of an enclosure.

16. A toe stretcher as set forth in claim 15, wherein the enclosure is selected from a group consisting of Velcro, snaps, an elastic band, hole and pin, and a male/female joint system.

17. A toe stretcher as set forth in claim 16, further comprising a footwear attached with the elongated bottom part.

18. A toe stretcher as set forth in claim 14, further comprising a footwear attached with the elongated bottom part.

19. A toe stretcher for stretching toes, comprising:
a frame with a separator for separating a plurality of toes;
wherein the frame has an elongated bottom part, and further includes:
a plurality of spacing members included in the elongated bottom part, thereby creating a plurality of indentations for placement of a plurality of toes, wherein:
at least one spacing member in the plurality of spacing members includes a vertical hole running from a top side of the at least one spacing member to a bottom side of the elongated bottom part, whereby a user may utilize the toe stretcher by placing a bottom side of at least one toe upon a corresponding indentation on the elongated bottom part and by placing at least one spacing member between adjacent toes, thereby placing the toe stretcher on the plurality of toes to effectively separate and stretch the toes.

20. A toe stretcher as set forth in claim 19, wherein a filament is placed through the vertical hole.

21. A toe stretcher as set forth in claim 20, wherein the filament is operative as an attachment, whereby a user may place the attachment over a top side of at least one toe and thereby utilize the toe stretcher.

22. A toe stretcher as set forth in claim 21, further comprising a footwear attached with the elongated bottom part.

23. A toe stretcher as set forth in claim 19, further comprising a footwear attached with the elongated bottom part.

* * * * *